United States Patent [19]

Westlund

[11] Patent Number: 5,749,911
[45] Date of Patent: May 12, 1998

[54] IMPLANTABLE TISSUE STIMULATOR INCORPORATING DEPOSITED MULTILAYER CAPACITOR

[75] Inventor: Randy W. Westlund, Minneapolis, Minn.

[73] Assignee: Cardiac Pacemakers, Inc., St. Paul, Minn.

[21] Appl. No.: 787,264

[22] Filed: Jan. 24, 1997

[51] Int. Cl.$^6$ ................................................ A61N 1/375
[52] U.S. Cl. .................................. 607/36; 607/2; 607/5
[58] Field of Search ................................ 607/36, 5, 4, 2

[56] References Cited

U.S. PATENT DOCUMENTS

| | | |
|---|---|---|
| 4,490,774 | 12/1984 | Olson et al. . |
| 4,499,520 | 2/1985 | Cichanowski . |
| 4,513,349 | 4/1985 | Olson et al. . |
| 4,515,931 | 5/1985 | Olson et al. . |
| 4,533,710 | 8/1985 | Olson et al. . |
| 4,586,111 | 4/1986 | Cichanowski . |
| 4,954,371 | 9/1990 | Yializis . |
| 5,032,461 | 7/1991 | Shaw et al. . |
| 5,097,800 | 3/1992 | Shaw et al. . |
| 5,125,138 | 6/1992 | Shaw et al. . |
| 5,131,388 | 7/1992 | Pless et al. ........................ 607/5 |
| 5,370,663 | 12/1994 | Lin . |
| 5,370,669 | 12/1994 | Daglow et al. . |
| 5,440,446 | 8/1995 | Shaw et al. . |
| 5,507,781 | 4/1996 | Kroll et al. ........................ 607/5 |
| 5,522,851 | 6/1996 | Fayram . |
| 5,527,346 | 6/1996 | Kroll . |

OTHER PUBLICATIONS

D.G. Shaw et al, "A New High Speed Process for Vapor Depositing Acrylate Thin Films: An Update", Society of Vacuum Costers, 36$^{th}$ Annual Technical Conference Proceedings (1993) pp. 348–352.

D.G. Shaw et al "Use of A High Speed Acrylate Deposition Process to Make Novel Multilayer Structures" Materials Research Society. vol. 382 pp. 77–82 (1995).

Primary Examiner—William E. Kamm
Assistant Examiner—Kennedy J. Schaetzle
Attorney, Agent, or Firm—Haugen and Nikolai, P.A.

[57] ABSTRACT

An implantable tissue stimulator includes a polymer film capacitor adhered to an inside wall surface of the stimulator's case or housing in a way that minimizes the size and weight of the stimulator device. The energy storage capacitor for the tissue stimulator comprises a monolithic, multilayer device and where the polymer is a suitable acrylate of a known formulation, over 1500 parallel plate capacitor electrodes can be built it with the height dimension of the resulting capacitor being less than about 3 mms. Instead of forming the capacitor on the inner surface of the stimulator's case in situ, such a capacitor can be formed on a mold member corresponding in shape to the inner surface of the stimulator's case and inserted into the stimulator's case following removal from the mold.

18 Claims, 10 Drawing Sheets

IMPLANTABLE TISSUE STIMULATOR INCORPORATING DEPOSITED MULTILAYER CAPACITOR

BACKGROUND OF THE INVENTION

I. Field of the Invention

This invention relates generally to implantable body tissue stimulating apparatus, and more particularly to an improved configuration for a capacitor used therein for periodically dumping a charge from a battery to tissue to be stimulated under control of an electronic switching circuit.

II. Discussion of the Prior Art

Implantable tissue stimulators of various types are known in the art for delivering electrical stimulating pulses to selected tissue structures. For example, cardiac pacemakers and implantable cardiac defibrillators have been developed for maintaining a desired pacing rate or for treating serious arrhythmias. While other tissue stimulating devices are known for treating a variety of conditions, the present invention will be described in relation to cardiac defibrillators, but it is not intended that the invention be limited to that particular application.

In its simplest form, an implantable cardiac defibrillator typically includes a metallic housing that is hermetically sealed and, therefore, impervious to body fluids. Contained within the housing is a battery power supply, electronic circuitry for detecting pathologic and/or non-pathologic arrhythmias and an electronic switching circuit for dumping a charge built up on a capacitor bank to cardiac tissue, via a set of defibrillating leads.

It is widely understood that life-saving implantable defibrillators need to be small. Making small devices that deliver large amounts of energy has typically been an inversely proportional relationship. The capacitors currently used in implantable defibrillators at least over the past ten years are typically cylindrical in shape. This shape and construction tends not to be volume efficient. There are spaces at the ends of each such cylindrical capacitor and along each side thereof that necessarily goes unused, limiting the ability to reduce the size of the housing. These spaces exist because the capacitor geometry transitions sharpely along corners and edges, while biocompatability requirements necessitate more gradual transitions in the housing to prevent it from causing tissue erosion at the implant site. The energy density and shape of the cylindrical capacitors significantly restricts the ability to design physiologically compatible housings that are extremely energy efficient.

Recent efforts have typically been made to fabricate flat, or cubic, capacitors (capacitors with a rectangular cross-section). These capacitors have been aluminum electrolytic in construction or ceramic, thin film or other known technologies. Like the cylindrical shape, the flat rectangular shape has the same inefficient abrupt corners and ends.

The Lin U.S. Pat. No. 5,370,663 discloses a capacitor construction for an implantable defibrillator which is intended to conserve space and allow a thinner profile than can be achieved using cylindrical or cubic capacitors. Here, a capacitor is formed by spirally winding elongated aluminum foil strips separated from one another by an insulating paper layer in an oval shape conforming somewhat to the oval shape of the metal housing of the defibrillator. The center portion of the helix is open and permits specially shaped, relatively flat batteries and circuitry to be inserted therein.

Another approach that purports to reduce the overall thickness dimension of an implantable defibrillator device is described in the Kroll U.S. Pat. No. 5,527,346. Here, relatively thin sheets of a suitable polymer that are first provided with a deposited metallic coating on the opposed surfaces thereof are stacked with separate intermediate thin polymer sheets as insulators to fabricate a capacitor of a desired capacitance value. Because of the fabrication techniques employed, the polymer thin film dielectric layers must have a thickness in the range of between 1 and 10 micrometers so as to be able to withstand the handling during fabrication of the capacitors. Films that are handled multiple times due to the processing steps involved, such as casting, stretching, slitting, metallizing, clearing and winding or stacking requires such layer thickness to withstand the stresses imposed during these operations. Films of lesser thickness are likely to have pinholes or other defects imparted to them due to processing stresses, leading to reduced voltage breakdown strength. Moreover, when attempting to work with films thinner than one micron one is presented with even greater difficulties in terms of processing and handling such thinner films. The Kroll patent attempts to minimize capacitor volume by utilizing a relatively high voltage and lower capacitance than is otherwise typically employed in cardiac defibrillating systems.

The Cichanowski U.S. Pat. No. 4,586,111 describes a capacitor construction with high volumetric efficiency in which a metal substrate has a base coat of a pre-polymer layer applied to it and this layer is then polymerized using electron beam bombardment. The polymerized layer is about 3–6 microns in thickness. Next, a vacuum deposited aluminum electrode of a thickness in the range of from 300 to 500 Angstroms is applied. The patent also suggests that monolithic multi-layer capacitors may be produced by depositing alternating electrode and dielectric layers so as to provide alternate electrode layers with portions projecting from the stack and contacting each other in electrically connected relation. The dielectric coating between each layer is preferably a polymer of polyacrylate which is formed by the vapor deposition of the pre-polymer and subsequent polymerization thereof.

Various techniques are known in the art for vapor depositing polyacrylates and, in this regard, reference is made to the Shaw et al. U.S. Pat. Nos. 5,440,446 and 5,032,461.

It is a principal object of the present invention to provide an improved capacitor arrangement in an implantable cardiac stimulating device that occupies significantly less volume while still permitting the device to deliver ample amounts of energy. An important benefit derived from the improved capacitor arrangement is the ability to design a housing having improved physiologic compatibility.

SUMMARY OF THE INVENTION

The present invention is an implantable tissue stimulating device having a hermetically sealed chamber defined by a metal housing, where the housing has an inner and an outer wall surface of a predetermined contour. Contained within the housing is a battery power supply, a capacitor means for storing a charge from the battery and an electronic switching means coupled to the capacitor means for periodically discharging said capacitor means into a tissue load. A particular feature of the device of the present invention is that the capacitor means comprises a multi-layer configuration preferably deposited in situ and occupying at least a portion of the inner wall surface of the housing. The capacitor's dielectric layers are an acrylate and the metal layers, preferably aluminum, but could be aluminum alloy, zinc or zinc alloy, are applied to the acrylate layers in a deposition process. Depending upon the copolymer used, the intermediate acrylate layers may have a thickness in a range from about 0.5 to 5 microns, and the metal layers may be in the range from about 200 to 500 Angstroms. Hence, a large multiplicity of the deposited acrylate and metallization layers occupy a relatively small volume and conform closely to the contours of the portion of the housing on which the deposited capacitor is adhered.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
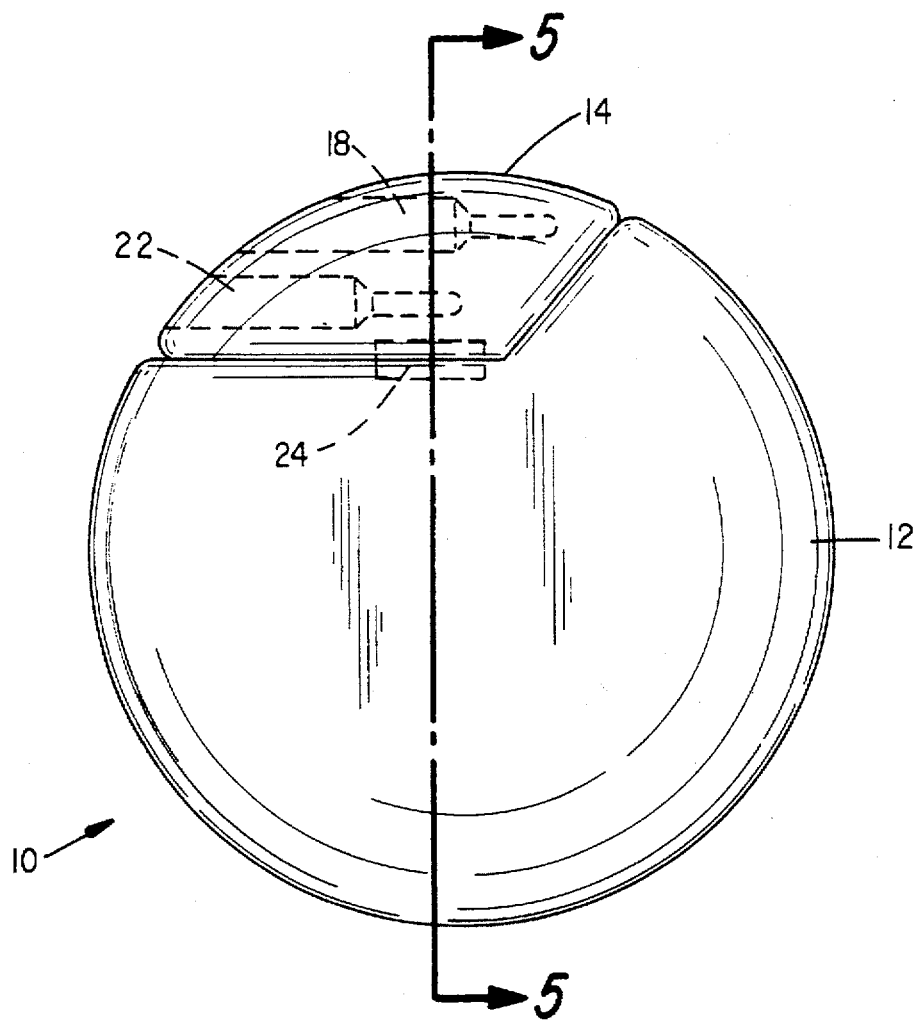
FIG. 1 is a side elevation of a cardiac stimulating device fabricated in accordance with a first embodiment of the present invention.

Referring first to FIG. 1, there is illustrated an implantable tissue stimulating device incorporating the present invention. The device is indicated generally by numeral 10 and includes a housing 12 formed from a suitable, body-compatible metal approved for medical use, such as titanium. In FIG. 1, the housing 12 is shown to be generally circular in its configuration, but those skilled in the art can appreciate that the housing will generally be shaped physiologically so as to avoid sharp edges which might lead to tissue necrosis following implantation.

Fitted on to the metal housing 12 and smoothly conforming to the generally circular configuration thereof is a molded plastic connector housing 14 having a plurality of bores as at 16, 18, 20 and 22 (FIG. 2) formed therein for receiving terminal pin connectors of one or more pacing/defibrillating leads (not shown) used to couple the tissue stimulator 10 to the tissue site to be stimulated. As is known in the art, the bores 16-22 contain contacts that mate with connector pins on the leads and the contacts are connected via hermetically sealed feed-throughs (not shown) that extend through a header 24 (FIG. 5) of the metal housing 12.

Figure 2:
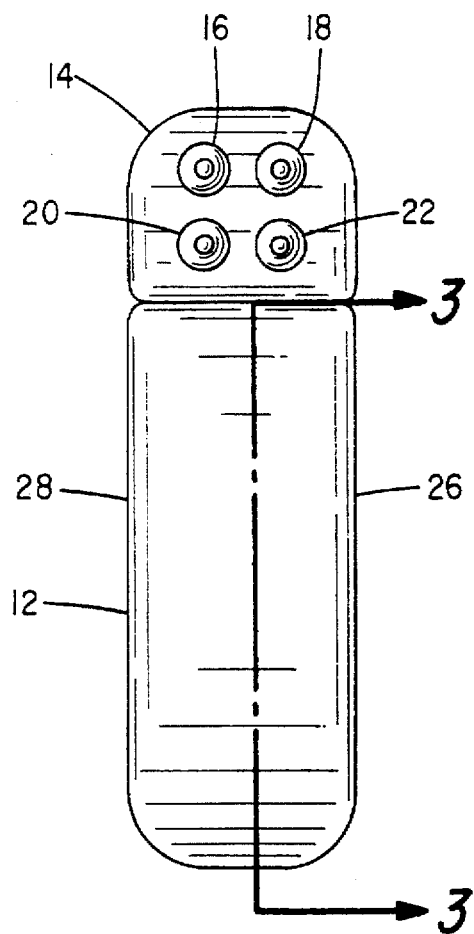
FIG. 2 is an edge view of the device of FIG. 1.

With reference to FIG. 2, the housing 12 will typically be formed from two can halves 26 and 28 that are welded together along a midline, such as is identified by 3—3 in FIG. 2.

Figure 5:
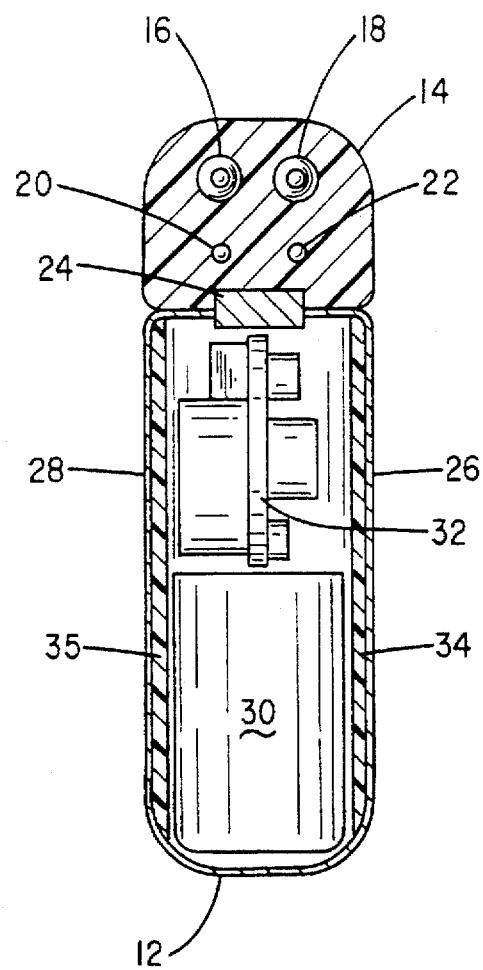
FIG. 5 is a cross-sectional view taken along the line 5—5 in FIG. 1 showing the arrangement of electronic components contained in the housing of the cardiac stimulating device.
Figure 6:
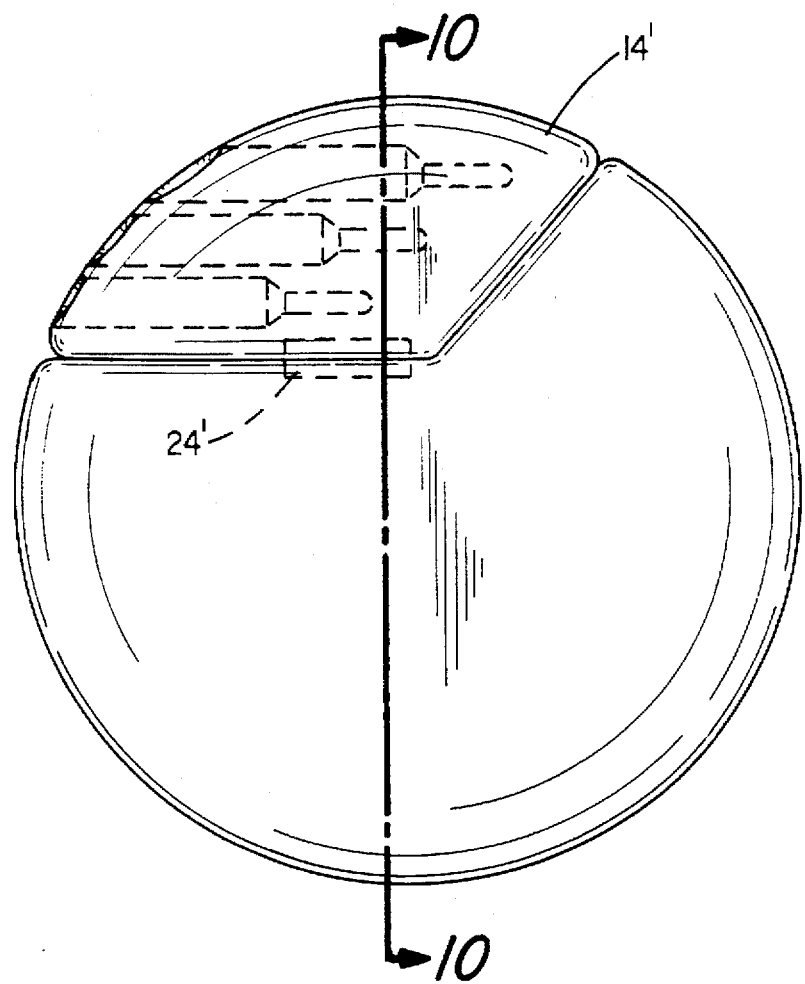
FIG. 6 is a side elevation of a cardiac stimulating device fabricated in accordance with the alternative embodiment of the present invention.

Next, with reference to the cross-sectional view of FIG. 5, it can be seen that there is contained within the housing 12 defined by the housing halves 26 and 28, the components implementing the tissue stimulating device. More particularly, the device 10 will normally include a battery type power supply 30 and one or more printed circuit boards, as at 32, on which is mounted the hybrid electronic components including discrete components and integrated circuitry. This circuitry will typically include a microprocessor based controller, a sense amplifier for processing cardiac signals picked up by the leads and a pulse generator for issuing tissue stimulating pulses under command of the microprocessor-based controller. In addition to the battery 30 and the hybrid-electronic circuitry, the implantable device will also include at least one energy storage capacitor, which in FIG. 5 is identified by numeral 34, and in accordance with the present invention, is preferably formed in situ as a monolithic capacitor on an inner wall surface of the housing half 26. Of course, a similar deposited monolithic capacitor 35 can also be disposed on the inner wall of housing half 28.

Figure 3:
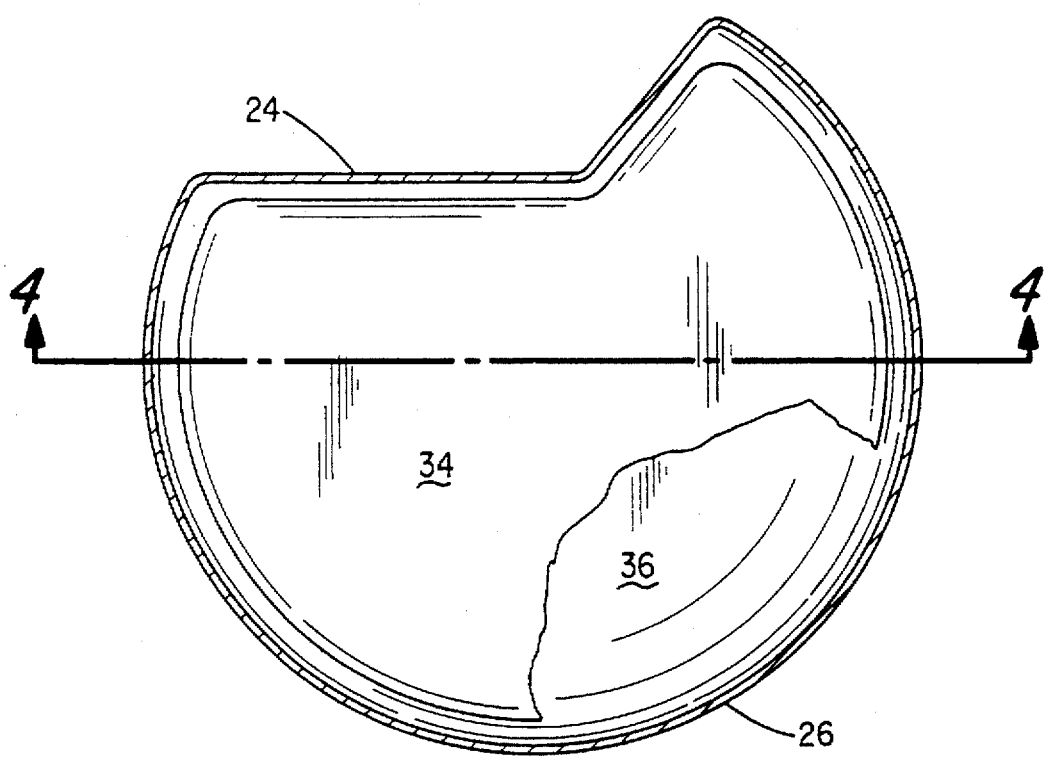
FIG. 3 is a cross-sectional view taken along the line 3—3 in FIG. 2 showing a deposited capacitor adhered to an inner wall of the device housing.

Referring next to FIG. 3, there is shown the inside wall surface 36 of the housing half 26 and formed thereon is the monolithic multi-layer energy storage capacitor 34. For a better explanation of the constructional features of the capacitor 34, reference is next made to the cross-sectional view of FIG. 4. Here, the housing half 26 functions as a substrate for the multi-layer deposited acrylate capacitor 34. More particularly, there is first formed on the inside surface 36 of the housing half 26 a base layer 38 of a suitable acrylate polymer or blend of polymers (co-polymer and tripolymers). The base layer may typically be of a thickness in a range between 50 and 100 microns and it is preferably built up by vacuum-depositing multiple coats of the acrylate polymer to thereby avoid pin-hole flaws therethrough. The base layer 38 is also able to withstand implant situations where the device case acts as one of the electrodes. Once the base layer 38 is applied and polymerized, a first electrode 40 is vacuum-deposited thereon. The electrode 40 will preferably comprise an ultra thin aluminum metal layer of a thickness in the range of from 100 to 500 Angstroms thick. Following that, a further layer of acrylate material 42 is deposited over the electrode 40 to a thickness preferably of about 0.5 to 2.5 microns in thickness.

Following formation of the intermediate layer 42 and its polymerization, a next metallic electrode 44 is vacuum-deposited on the intermediate layer 42, with these steps being repeated until a capacitor of desired design parameters is achieved.

Figure 4:
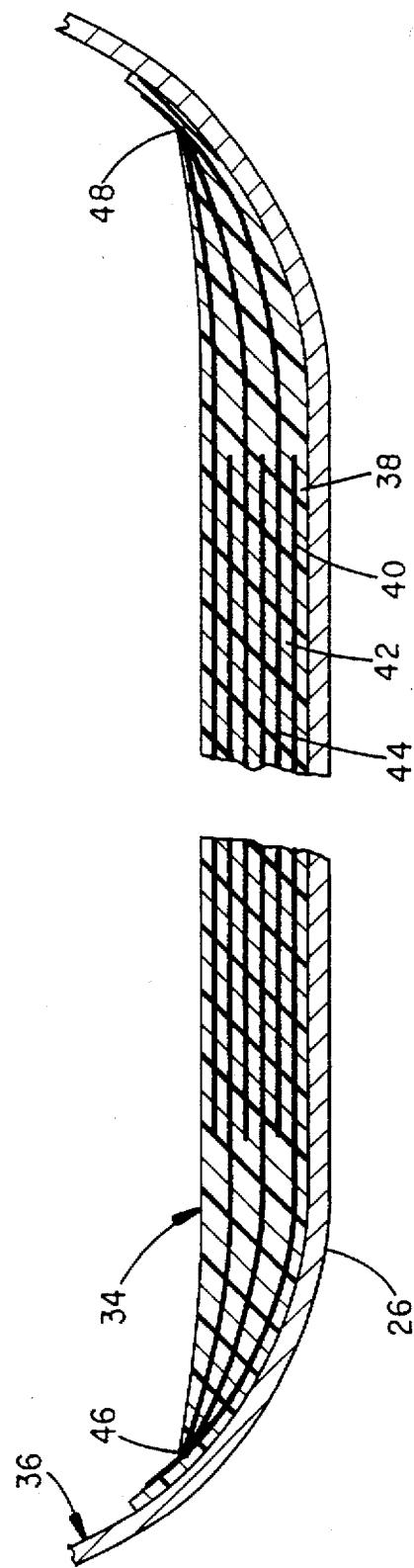
FIG. 4 is a greatly enlarged sectioned view taken along the line 4—4 in FIG. 3.

It is to be noted from FIG. 4 that the odd electrode layers 40, 44, etc. in the stack are brought out to a first terminal point 46 and the even numbered electrodes in the stack are electrically connected in common to another terminal point 48, thus defining the two terminals of the monolithic capacitor.

Various methods are known in the art for depositing monolithic capacitors on a substrate. In this regard, reference is made to the Yializis U.S. Pat. No. 4,954,371 and the Shaw et al. U.S. Pat. No. 5,125,138. Further information on applicable processes are described in an article entitled "A New High Process for Vapor Depositing Acrylate Thin Films: An Update" by D. G. Shaw et al., published in the 36th Annual Technical Proceedings of the Society of Vacuum Coaters (1993), pp. 348–352, the teachings of which are hereby incorporated by reference as if fully set forth.

Using the approach of this invention, a high energy density capacitor can be incorporated on the inside surface of the case or housing of a tissue stimulating device such as a defibrillator or pacemaker. The multiple layers of acrylate are laid up on the internal surface, be it flat or arcuate, to form a capacitor capable of being charged up to a suitable voltage in the range of from 100 to 900 volts for a defibrillator depending on the type of arrhythmia being addressed. Similarly, the capacitor for a defibrillator may exhibit a capacitance value ranging from 60 microfarads to 140 microfarads or higher. Capacitors of these voltage ratings and capacitance values may be created by laying down about 1500 electrode layers which project inward by a depth dimension of only about 3 mm. An important benefit of the thin film deposited capacitor technology as applied to implantable devices is that the capacitor can be tailored to a given application. For example, if it is desired to have, say, 32 joules delivered to the heart in response to the detection of ventricular fibrillation, the internal dielectric layers would be made thicker to handle the 700 to 900 volts typically required. However, if atrial fibrillation is to be treated with an implantable defibrillator, a defibrillating shock of only three joules may be needed. Here, the capacitor would be designed to handle about 200 volts. Similarly, if the implantable device is to address ventricular fibrillation with a combination of low energy pre-shocks and larger subsequent post-shocks, multiple capacitors connected in parallel or in series/parallel configuration may be incorporated into the device which are tailored for the desired energies and voltages.

As previously indicated, if the capacitor energy requirements dictate, it is possible to form capacitors on both housing halves 26 and 28 as shown in FIG. 5. By forming two such capacitors, one on each housing half, it would be possible to interconnect them either in series or in parallel depending upon device requirements. By always making sure that the outermost layer of the energy storing capacitors is the acrylate material, the circuitry contained on the printed circuit board 32 will be electrically insulated from the inside walls of the two housing halves.

Figure 7:
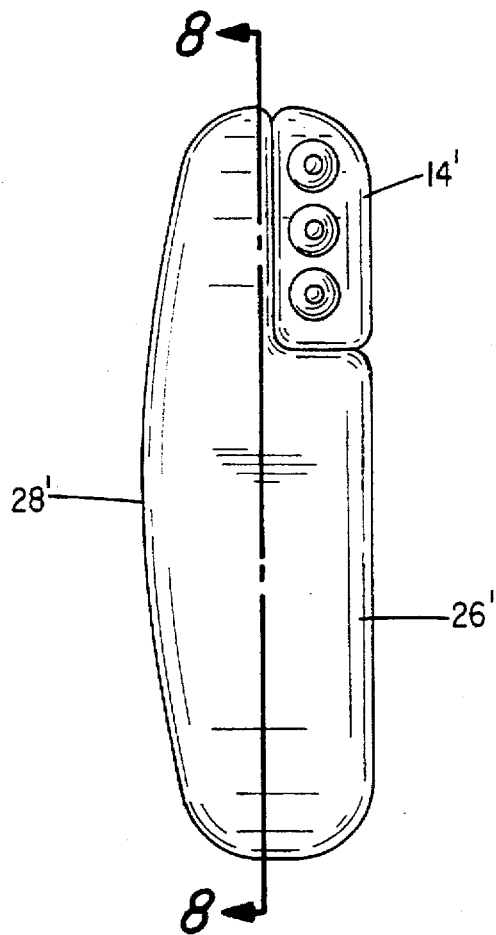
FIG. 7 is an edge view of the device of FIG. 6.
Figure 8:
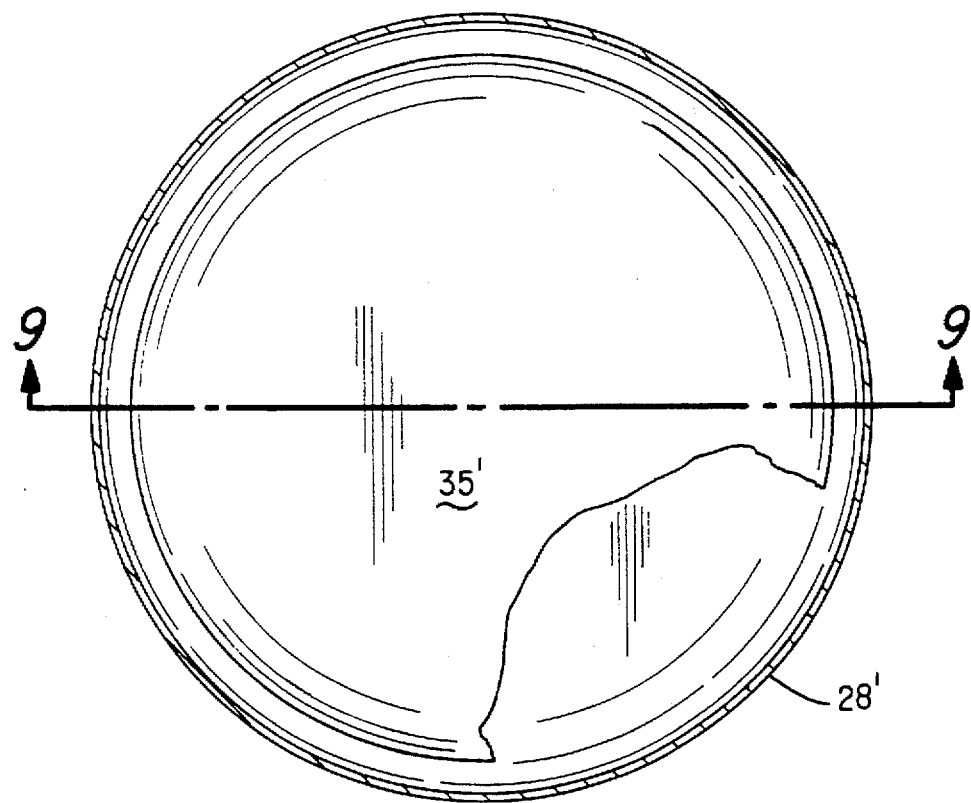
FIG. 8 is a cross-sectional view taken along the line 8—8 in FIG. 7 showing a deposited capacitor adhered to an inner wall of the device housing.
Figure 9:
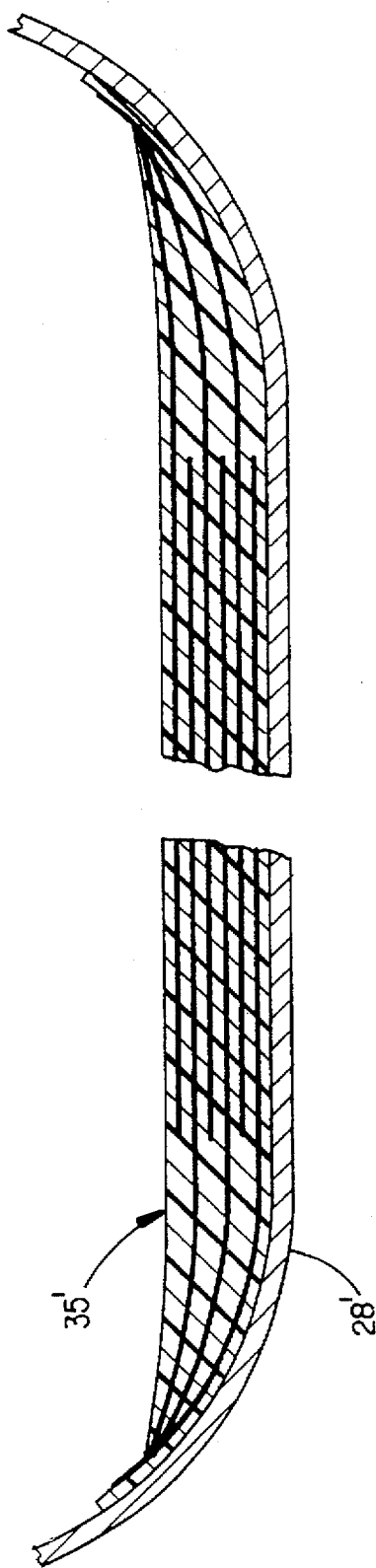
FIG. 9 is a greatly enlarged sectioned view taken along the line 9—9 in FIG. 8.
Figure 10:
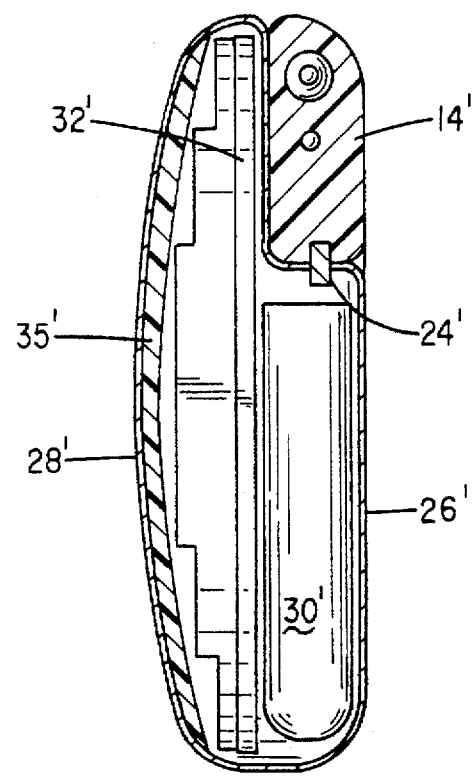
FIG. 10 is a cross-sectional view taken along the line 10—10 in FIG. 6 showing the arrangement of electronic components contained in the housing of the cardiac stimulating device.

The implantable stimulator depicted in FIGS. 1 through 5 of the drawings represent the general shape configuration of the state-of-the-art implantable devices. FIGS. 6 through 10 depicts a more physiologic shape of the implantable device made possible by the present invention. As can best be seen in the edge view of FIG. 7, by substituting vacuum-deposited monolithic acrylate capacitors for conventional, cylindrical or rectangular capacitors, a generally thinner and more smoothly rounded profile can be used on the housing half 28'. In this embodiment, the header 24' and connector housing 14' extend only across the thickness dimension of a single housing half 26' as best seen in FIGS. 7 and 10. The housing half 28' thus has an increased area for supporting a larger deposited acrylate capacitor 35'. Moreover, the thinner, gently rounded, lighter weight construction tends to be more physiologically compatible with the body for either pectoral or abdominal siting. The constructional features of the monolithic capacitor illustrated in FIG. 9 is generally identical to that shown in FIG. 4 and already described. Hence, further explanation of the constructional features of the monolithic capacitor or capacitors used in the embodiment of FIGS. 6 through 10 is deemed unnecessary.

It is not necessary to limit the placement of the capacitor to the planar portions of the case halves in that when using a vacuum deposition technique for applying both the acrylate insulating material and the aluminum capacitor plates, those materials will conform to the shape characteristics of the housing, thus further improving the packaging efficiency/density of the device, especially when contrasted to prior art implantable stimulating devices incorporating cylindrical or cubic energy storage capacitors.

A further advantage of the formation of the energy storage capacitors on the inner wall of the can or housing resides in the inherent physical properties of tightly cross-linked acrylates. The physical strength of the acrylate, after processing, is sufficient to lend additional rigidity to the housing itself. That is to say, when a sufficient amount of acrylate is deposited on the inside surfaces of the can for high energy storage capacitor purposes, it also increases the strength of the case halves. This permits reduction in the thickness of the walls of the metal housing. For example, existing state-of-the-art pacemakers/defibrillators have a titanium case whose thickness is typically about 0.016 inch so as to provide both a hermetically sealed enclosure impervious to body fluids and physical protection to the electronic circuits contained within it. By adhering the acrylate capacitors to the inner surfaces of the housing, the can material thickness can be reduced to about 0.006 to 0.008 inches. This represents approximately a 2–3 cubic centimeter reduction in volume and a 10–12 gram reduction in the weight from the present day designs.

By way of summary, the present invention provides an improved construction of an implantable tissue stimulating device by the formation of a monolithic vacuum deposited capacitor on the inside walls of the can or housing that provides the hermetic seal for the electronics involved. Inherent in the present invention are the following advantages:

1. The energy storage capacitor(s) are integrated into the device case.
2. The capacitor is tolerant of most any device shape.
3. The capacitor construction maximizes the device's packaging efficiency by taking advantage of unused and difficult to use spaces.
4. The monolithic deposited flat acrylate capacitor(s) allows reduction in device volume and weight due to the structural nature of the capacitor and potential for reduction in the metal thickness of the case or housing.
5. The coating technique employed in formation of the monolithic energy storage capacitor(s) offers electrical protection and isolation between the inside housing surface and all internal components.
6. The fabrication technique involved provides an ability to segregate and customize energy sources for different arrhythmia therapies.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims. For example, one such variation that comes to mind would involve formation of the acrylate multi-layer capacitor on a reusable mold having the same shape configuration as the inner surfaces of the stimulator's housing followed by removal of the finished capacitor from such mold and the placement thereof into the stimulator's housing at the location conforming to the shape of the mold.

What is claimed is:

1. A tissue stimulating device comprising:
   (a) a hermetically sealed chamber defined by a metal housing, the housing having inner and outer wall surfaces of a predetermined contour;
   (b) a battery disposed within the sealed chamber;
   (c) capacitor means for storing a charge;
   (d) an electronic circuit means coupled to said capacitor means for periodically discharging said capacitor means into a tissue load; and
   (e) said capacitor means comprising a multilayer configuration of alternating dielectric and metal layers including an acrylate base layer deposited, in situ, on and conforming to at least a portion of the inner wall surface of the housing.

2. The tissue stimulating device as in claim 1 wherein the capacitor means conforms to the predetermined contour of the portion of the inner wall surface on which the acrylate base layer is disposed.

3. The tissue stimulating device as in claim 1 wherein the acrylate base layer has a thickness in a range from about 50 microns to 100 microns.

4. The tissue stimulating device as in claim 1 wherein the metal of the metal layers are selected from the group consisting of aluminum, zinc, aluminum alloys and zinc alloys and are separated from one another by intermediate layers of acrylate.

5. The tissue stimulating device as in claim 4 wherein the intermediate layers of acrylate have a thickness in a range from about 0.5 to 2.5 microns and the metal layers are aluminum and have a thickness in a range from about 200 to 500 Angstroms.

6. The tissue stimulating device of claim 1 wherein the predetermined contour of the portion of the inner wall surface on which the acrylate base layer of the capacitor means is deposited is arcuate.

7. The tissue stimulating device as in claim 1 wherein the predetermined contour of the portion of the inner wall surface on which the acrylate base layer of the capacitor means is deposited is planar.

8. The tissue stimulating device as in claim 1 wherein the metal housing is titanium and has a wall thickness in a range of from about 0.006 to 0.010 inches with the capacitor means adhering to the inner wall surface providing structural rigidity to the housing.

9. The tissue stimulating device as in claim 1 wherein the acrylate base layer provides electrical isolation between the metal housing and the electronic circuit means.

10. An implantable tissue stimulating device comprising:
    (a) a hermetically sealed chamber defined by a metal housing, the housing having inner and outer wall surfaces of a predetermined contour;
    (b) a battery disposed within the sealed chamber;
    (c) a plurality of capacitors for storing charges thereon;
    (d) means for connecting said plurality of capacitors together in a predetermined series/parallel relationship;
    (e) electronic circuit means coupled to the connecting means for periodically discharging said plurality of capacitors into a tissue load; and
    (f) said plurality of capacitors each comprising a multilayer configuration of alternating dielectric and metal layers including an acrylate base layer deposited, in situ, on at least a portion of the inner wall surface of the housing.

11. The tissue stimulating device as in claim 10 herein the capacitor means conforms exactly to the redetermined contour of the portion of the inner wall surface on which the multi-layer configuration is deposited.

12. The tissue stimulating device as in claim 10 wherein the acrylate base layer has a thickness in a range from about 50 microns to 100 microns.

13. The tissue stimulating device as in claim 10 wherein the metal of the metal layers are selected from the group consisting of aluminum, zinc, aluminum alloys and zinc alloys and are separated from one another by intermediate layers of acrylate.

14. The tissue stimulating device as in claim 13 wherein the intermediate layers of acrylate have a thickness in a range from about 0.5 to 2.5 microns and the metal layer are vacuum deposited on the intermediate layers of acrylate and have a thickness in a range from about 200 to 500 Angstroms.

15. The tissue stimulating device of claim 10 wherein the predetermined contour of the portion of the inner wall surface on which the capacitor means is deposited is arcuate.

16. The tissue stimulating device as in claim 10 wherein the predetermined contour of the portion of the inner wall surface on which at least one of the plurality of capacitors is deposited is planar.

17. The tissue stimulating device as in claim 10 wherein the metal housing is titanium and has a wall thickness in a range of from about 0.006 to 0.010 inches with the plurality of capacitors adhering to the inner wall surface providing structural rigidity to the housing.

18. The tissue stimulating device as in claim 10 wherein the acrylate base layer provides electrical isolation between the metal housing and the electronic circuit means.

* * * * *